United States Patent
Themelis (10) Patent No.: US 11,501,427 B2
(45) Date of Patent: Nov. 15, 2022

(54) MEDICAL IMAGING APPARATUS AND METHOD FOR THE IMAGING OF A LIGHT-SENSITIVE OBJECT, SUCH AS BIOLOGICAL TISSUE

(71) Applicant: LEICA INSTRUMENTS (SINGAPORE) PTE. LTD., Singapore (SG)

(72) Inventor: George Themelis, Lindau (DE)

(73) Assignee: LEICA INSTRUMENTS (SINGAPORE) PTE. LTD., Singapore (SG)

( * ) Notice: Subject to any disclaimer, the term of this patent is extended or adjusted under 35 U.S.C. 154(b) by 13 days.

(21) Appl. No.: 15/642,726

(22) Filed: Jul. 6, 2017

(65) Prior Publication Data

US 2018/0033141 A1 Feb. 1, 2018

(30) Foreign Application Priority Data

Jul. 29, 2016 (EP) ..................................... 16181848

(51) Int. Cl.
*G06K 9/00* (2022.01)
*G06T 7/00* (2017.01)
(Continued)

(52) U.S. Cl.
CPC .......... *G06T 7/0012* (2013.01); *A61B 3/0025* (2013.01); *A61B 3/0041* (2013.01);
(Continued)

(58) Field of Classification Search
CPC ....... A61B 3/0025; A61B 3/0041; A61B 3/12; A61B 3/14; G06T 2207/30041; G06T 7/0012
See application file for complete search history.

(56) References Cited

U.S. PATENT DOCUMENTS 6,089,716 A * 7/2000 Lashkari .............. A61B 3/1241
351/205
6,792,136 B1 9/2004 Niesen
(Continued)

FOREIGN PATENT DOCUMENTS

CN 204813796 U 12/2015
EP 2189108 A1 5/2010
(Continued)

*Primary Examiner* — Sean M Conner
(74) *Attorney, Agent, or Firm* — Hodgson Russ LLP (57) ABSTRACT

A medical imaging apparatus (1) and method for imaging a light-sensitive object (2), such as tissue (3) of the eye (4), displays the object (2) in spectral bands (30) of the visible light range (37) in which the object is sensitive and cannot be illuminated. The apparatus (1) has a camera (8) for capturing input images (10) in which a spectral signature (36) of the object is represented by an input set (15) of spectral bands (16). The apparatus generates output images (22) in which the spectral signature (60) in the visible light range (37) is represented by an output set (29) of spectral bands (30). Replacing at least one input-only spectral band (38) in the input set (15) by at least one output-only spectral band (39) in the output set (29) enables capture of input images (10) in spectral bands (16) where the object (2) has less sensitivity, such as in the non-visible light-range (18), and display of the object (2) in spectral bands (30) where the object would be too sensitive for illumination (40).

12 Claims, 2 Drawing Sheets

(51) Int. Cl.
*A61B 3/14* (2006.01)
*A61B 3/12* (2006.01)
*A61B 3/00* (2006.01)

(52) U.S. Cl.
CPC ............ *A61B 3/12* (2013.01); *A61B 3/14* (2013.01); *G06T 2207/30041* (2013.01)

(56) References Cited

U.S. PATENT DOCUMENTS

| | | | |
|---|---|---|---|
| 8,428,320 B2* | 4/2013 | Diem | G06T 7/0012 |
| | | | 382/128 |
| 8,724,894 B1 | 5/2014 | Jensen et al. | |
| 8,810,651 B2* | 8/2014 | Calnegru | H04N 9/045 |
| | | | 348/143 |
| 9,380,270 B1* | 6/2016 | Worley, III | G06K 9/2018 |
| 2001/0021271 A1* | 9/2001 | Ishibashi | G06T 9/007 |
| | | | 382/232 |
| 2003/0021472 A1* | 1/2003 | Nichogi | H04N 19/172 |
| | | | 382/166 |
| 2007/0016079 A1* | 1/2007 | Freeman | G16H 50/20 |
| | | | 600/476 |
| 2008/0157000 A1* | 7/2008 | Shamir | G02B 23/12 |
| | | | 250/473.1 |
| 2009/0326383 A1* | 12/2009 | Barnes | H04N 5/2256 |
| | | | 600/476 |
| 2010/0056928 A1* | 3/2010 | Zu | A61B 5/0071 |
| | | | 600/476 |
| 2010/0166330 A1* | 7/2010 | Thyagarajan | G06K 9/2018 |
| | | | 382/250 |
| 2010/0245765 A1* | 9/2010 | Dyer | A61B 3/13 |
| | | | 351/206 |
| 2011/0151575 A1* | 6/2011 | Fraser | G01J 3/02 |
| | | | 436/155 |
| 2011/0273550 A1* | 11/2011 | Amano | A61B 3/10 |
| | | | 348/77 |
| 2013/0272617 A1* | 10/2013 | Conger | G06K 9/2018 |
| | | | 382/225 |
| 2013/0342845 A1* | 12/2013 | Chen | G01J 3/32 |
| | | | 356/419 |
| 2014/0112559 A1* | 4/2014 | Freeman | A61B 5/145 |
| | | | 382/128 |
| 2015/0015692 A1* | 1/2015 | Smart | G01J 3/51 |
| | | | 348/77 |
| 2015/0044098 A1* | 2/2015 | Smart | G01J 3/2823 |
| | | | 422/82.05 |
| 2015/0230875 A1* | 8/2015 | Shad | G06F 19/00 |
| | | | 600/407 |
| 2016/0015470 A1* | 1/2016 | Border | A61B 5/1103 |
| | | | 600/117 |
| 2016/0093056 A1* | 3/2016 | Ouzounis | G06K 9/6282 |
| | | | 382/224 |
| 2016/0150213 A1* | 5/2016 | Mutti | G06K 9/4604 |
| | | | 348/143 |
| 2017/0262984 A1* | 9/2017 | Barnes | G06T 7/11 |
| 2018/0197052 A1* | 7/2018 | Yanson | G06K 19/0614 |
| 2018/0308260 A1* | 10/2018 | Robles-Kelly | G01J 3/2823 |

FOREIGN PATENT DOCUMENTS

| | | |
|---|---|---|
| JP | 2002543863 A | 12/2002 |
| JP | 2009285447 A | 12/2009 |
| JP | 2010233916 A | 10/2010 |
| WO | 2011155136 A | 12/2011 |

* cited by examiner

MEDICAL IMAGING APPARATUS AND METHOD FOR THE IMAGING OF A LIGHT-SENSITIVE OBJECT, SUCH AS BIOLOGICAL TISSUE

CROSS REFERENCE TO RELATED APPLICATIONS

This application claims priority of European patent application number 16181848.9 filed Jul. 29, 2016, the entire disclosure of which is incorporated by reference herein.

FIELD OF THE INVENTION

The invention relates to a medical imaging apparatus and method for the imaging of a light-sensitive object having a spectral signature, for example biological tissue, in particular light-sensitive tissue of a living body, such as of an eye. The medical imaging apparatus and method in particular are an ophthalmologic apparatus and method, respectively.

BACKGROUND OF THE INVENTION

The observation and imaging of objects such as living tissue is complicated if the object is light-sensitive. Light-sensitivity may cause the tissue to react if illuminated. This reaction may cover characteristics of the tissue that need to be observed to make a diagnosis. In some instances, the illumination may even damage the tissue.

In ophthalmology, the sensitivity of the light-sensitive tissue in the eye results in discomfort for the patient, a higher risk of injury and additional difficulties due to the eye's reflex reaction to light.

To avoid these problems, color cameras are used which produce an acceptable image quality at low light conditions. Such cameras are, however, expensive and bulky and need expensive and large high-quality optics. The large aperture of the optics, which is needed to capture as much of the incoming light as possible, leads only to a limited depth of the field of view.

SUMMARY OF THE INVENTION

The present invention aims to provide a medical imaging apparatus and method which overcomes these problems in the examination of living light-sensitive tissue.

For the medical imaging apparatus initially mentioned, this objective is achieved according to the invention in that the medical imaging apparatus comprises a camera for capturing input images, the spectral signature of the object being represented in the input images by an input set of spectral bands, an output interface for transmitting output images, e.g. to a peripheral device, wherein, in the output images, the spectral signature in the visible light range is represented by an output set of spectral bands, wherein at least one input-only spectral band in the input set is replaced by at least one output-only spectral band in the output set, the medical imaging apparatus further comprising a storage member, in which calibration data are stored for mapping the input set to the output set of spectral bands, and an image processor for determining an intensity in the at least one output-only spectral band depending on the input set and the calibration data.

The medical imaging method according to the invention comprises the steps of acquiring input images in an input set of spectral bands, transmitting output images including an output set of spectral bands, the output set representing the spectral signature in the spectral bands of the output set, converting the input images to the output images by replacing at least one input-only spectral band in the input set by at least one output-only spectral band in the output set and adapting the intensity in the at least one output-only spectral band to the spectral signature using previously stored calibration data.

The invention uses the information which is contained in the input set of spectral bands to determine the spectral signature of the object and to render the spectral signature in the output images using an output set of spectral bands which differs from the input set. This allows to record images in spectral bands at which the object, in particular the sensitive tissue, does not have any sensitivities, e.g. in the IR or NIR range. Using the calibration data, the "true" spectral signature of the object is rendered using the spectral bands of the output set in a spectral range, e.g. the visible light range, which is different from the spectral range in which the input images are captured.

If the output images are displayed on a display the observer would see the very same colors as if observing the tissue in the output set of spectral bands. Thus, imaging is done in a spectral range which is not critical for the tissue e.g. by being invisible to the human eye, whereas displaying is done in the visible-light range to allow the observer proper identification of the tissue by its natural color.

The method and apparatus according to the invention have the advantage of lessened discomfort for the patient and significantly reducing the risk of injury to the tissue. The inventive method and apparatus allow for significantly longer examinations, which helps to prevent errors in diagnosis and therapy.

The apparatus and method may also be used outside medical applications. For example, in military applications, it may be possible to watch an object in ambient light that has only a restricted number of spectral bands with sufficient intensity. Using the invention allows to display the object in its natural colors.

The method and apparatus according to the invention can be further improved by the following features, which are independent of one another with respect to their respective technical effects and which can be combined arbitrarily.

For example, it is preferred that at least two spectral bands of the input set, termed input spectral bands in the following, are in the longer non-visible wavelengths, in particular the IR light range. Especially in ophthalmology, the tissue is significantly less sensitive in the longer non-visible wavelengths compared to the shorter non-visible wavelengths, i.e. UV. However, shorter wavelengths, in blue and or UV spectral bands, could also be used, especially for the study of superficial tissue layers, due to low penetration of shorter wavelength light.

The input images and the output images may be part of a time-series of input images and output images which are captured and/or displayed at a frame rate which is higher than the flicker fusion rate so that any change in the tissue during observation can be smoothly rendered in the output images.

The input images may contain input pixels. The output images may contain output pixels. The input images may be color images. The output images may be color images.

According to one aspect, each input pixel represents a location in the field of view of the camera. Preferably, the output images and input images are congruent and have the same orientation. They may have the same resolution, amount of pixels, size and/or aspect ratio. Preferably, an input pixel in the input image and an output pixel in the output image represent the same, or at least an overlapping, location in the field of view or the same area of the observed tissue, respectively.

The conversion from the input set to the output set is preferably performed on a pixel base: For each pixel in the input image, the corresponding intensities in the output-only spectral bands are computed depending on the intensities in the input spectral bands and the calibration data.

According to another advantageous embodiment of the invention, the medical imaging apparatus may comprise an illumination system for illuminating the object with light including an illumination set of spectral bands. The illumination spectral bands may be bands at least partly in the non-visible light range, in particular in at least the input spectral bands. The output-only spectral band preferably is attenuated or not present in the illumination set. The illumination of the tissue in the input spectral bands ensures a good quality of the input images with respect to depth of field and spatial resolution without the need for special low-light optics or cameras. In the input spectral bands, there is no risk of injuring the tissue or putting the patient in discomfort. Further, in ophthalmological examinations, the eye will not react to an illumination in the non-visible light range by contracting the iris thus allowing for an easier inspection.

In other applications outside medicine, such an illumination may prohibit detection of the illumination source.

Preferably, the illumination is restricted to the non-visible light range. For example, an illumination filter may be provided that restricts illumination of the tissue to the non-visible light range.

As illumination is needed only in the input spectral bands, it is sufficient if the illumination is restricted to the input spectral bands. Thus, the illumination filter can comprise a band-pass filter and/or a band-stop filter system that is transmissive in the input spectral bands.

The illumination may, according to another aspect of the invention, comprise preferably discrete illumination spectral bands which match the input spectral bands of the multispectral camera. The input spectral bands and the illumination spectral bands may be constituted by light having a wavelength of at least 550 nm. In particular, the illumination system may comprise an IR and/or NIR light source.

To avoid irritation of the eye or any other type of interference with the object, the majority, if not all, of the input-only spectral bands is in one embodiment located outside the visible light range, in particular the IR or NIR range, whereas the majority, if not all, of the output-only spectral bands is in the visible light range. The input and/or output spectral bands may be discrete and/or have a substantial overlap. A majority, if not all, of the spectral bands in the input set may be located in the non-visible light range to gather as much information about the spectral signature of the object in the non-sensitive spectral bands as possible. For optimum rendition of the colors of the object, the majority, if not all, of the spectral bands in the output set may be in the visible light range.

The camera may be an imaging spectroscope, in particular a multispectral camera or a hyperspectral camera. The more spectral bands used, the better the spectral resolution of the input spectral signature and the more accurate the assignment of the spectral signature of the object to the output set will be. For some applications a standard color camera e.g. operating the RGB color space may be sufficient.

The output set may comprise in one embodiment only three preferably discrete spectral bands and may in particular be composed by a tri-color color space, such as RGB. Such a color system is sufficient for the output pixels to render the true color of the tissue faithfully for a human observer.

According to another aspect of the invention, the image processor may be configured to transform the input set into the RGB space. Here, the output set comprises the R-, G- and B-spectral bands. Theoretically, this is an ill-posed problem and cannot be solved, because the spectral signature in the input set alone does not contain enough information to determine the color appearance of the tissue in the spectral bands outside the input set. However, prior knowledge of the optical, e.g. reflective, properties of the biological tissue can offer the additional information required to calculate this transformation. This information is contained in the calibration data.

The image processor may be configured to classify the tissue represented by an input pixel depending on the input spectral signature by spectral fitting. The image processor may comprise a spectral analysis module for performing a spectral fitting to the input spectral signature and for computing a tissue reference value from the spectral fitting, wherein the image processor is configured to determine the output spectral signature in dependence of the tissue reference value. Thus, the spectral analysis module may perform a classification of the tissue represented by an input pixel. Classification can be done by assigning the tissue reference value to an individual input spectral signature. This numerical value is then characteristic for a special kind of tissue, e.g. for a tissue having a particular concentration of biological pigments. By determining the output spectral signature in dependence of the tissue reference value, the visual appearance of the tissue in the visible light range can be matched to the tissue having a particular input spectral signature in the non-visible light range. The tissue reference value is representative for the color of the tissue in the visible-light range.

The calibration data may comprise a spectral library. The spectral library may be indexed using the tissue reference value. Each of the multitude of output spectral signatures may be assigned to a unique respective tissue reference value.

The calibration data may comprise parameters of a transfer function which maps the input set onto the output set. Such transfer functions may be determined empirically or analytically, e.g. based on light-tissue interaction models.

The calibration data may comprise parameters of a machine learning system, e.g. a neural network, which was trained with model input and output sets.

The tissue reference value can be anything from a single bit to a bit field, it can be, in a particular instance, a single numerical value or an array of numerical values. It may represent one or more quantities, such as exponents of an exponential Fourier series, or RGB values. The tissue reference value may further be an array of numerical values which indicates the concentration of biological pigments contributing to and/or resulting in the input spectral signature. Such an array can be used to construe the output spectral signature in the visible-light image from model output spectral signatures in a spectral library, where each output spectral signature represents the color of a constituent biological pigment in the visible-light range.

If the concentration of the biological pigments in the tissue is determined automatically from the input spectral signature of the input pixel, e.g. by the above-mentioned spectral fitting, the output spectral signature may be composed from the model output spectral signatures depending on the concentration. The biological pigments of which the concentration is determined and/or which model output spectra are stored in the spectral library, comprises at least one of oxy-hemoglobin, deoxy-hemoglobin and at least one melanin such as eumelanin. Preferably, the number of input spectral bands is at least as large as the number of biological pigments represented in the spectral library.

Instead of such a composition of the output spectral signature from a plurality of model output spectral signatures, the output spectral signatures can also be looked up directly in a differently configured spectral library.

In order to perform the spectral fitting, the storage member may, in another embodiment, comprise representations of model input spectral signatures of certain biological pigments, such as the above, stored for spectral fitting the input spectral signature of the input pixels.

The image processor and any module comprised by the image processor may be constituted by hardware and/or software.

The invention may also relate to a non-transitory computer storage medium storing a program causing a computer to execute the medical imaging method in one of the embodiments described above. The non-transitory computer storage media may be part of the medical imaging apparatus.

In the following, the method and apparatus according to the invention are explained in greater detail with reference to the accompanying drawings, in which exemplary embodiments are shown.

In the Figures, the same reference numerals are used for elements, which correspond to each other in their function and/or structure.

According the description of the various aspects and embodiments, elements shown in the drawings can be omitted if the technical effects of these elements are not needed for a particular application. Vice versa, elements that are not shown or described with reference to the Figures, but are described above, can be added if the technical effect of that particular element is advantageous in a specific application.

BRIEF DESCRIPTION OF THE DRAWING VIEWS

In the Figures.

DETAILED DESCRIPTION OF THE INVENTION

First, an example of a medical imaging apparatus 1 is described with reference to FIG. 1.

The medical imaging apparatus 1 is used for the imaging of an object 2, such as biological tissue 3, in particular light-sensitive regions of tissue, such as in an eye 4. The medical imaging apparatus 1 is in particular used in ophthalmology as an ophthalmological imaging device 6.

The medical imaging apparatus 1 comprises a camera 8 for capturing input images 10 of the tissue 3 located in a field of view 12. The camera 8 may be a color camera such as an RGB camera or an imaging spectrograph such as a multi-spectral or a hyperspectral camera.

Each input image 10 comprises input pixels 14. Each pixel 14 represents a region of the field of view. Each input image 10 and each input pixel 14, respectively, contains an input set 15 of at least spectral bands 16.

The camera 8 is sensitive in the at least two discrete input spectral bands 16 in the non-visible light-range 18. The non-visible light consists of the portion of the electromagnetic spectrum that is not visible to the human eye. The spectral bands of the non-visible light-range 18 thus correspond to wavelengths of less than about 390 nm or more than about 700 nm. It is preferred that the at least two spectral bands are located in the infrared or near-infrared and thus comprise wavelengths of more than 700 nm to about 1 mm.

The medical imaging apparatus 1 further comprises a preferably digital output interface 20 for transmitting output images 22 preferably digitally to a peripheral device 24, such as a display. The display 24 displays the output images 22 in the visible-light range having wavelengths between about 390 nm and about 700 nm.

The output images 22 are color images and comprise output pixels 26. The output images 22 may have a standardized color space format, and be for example RGB images.

The input images 10 and the output images 22 are preferably congruent and rectified. The input pixels 14 and the output pixels 26 are preferably congruent. Thus, the location of the output pixel 26 within the output image 22 corresponds to the location 28 of a respective input pixel 14 in the field of view 12. Each input pixel 14 contains spectral information of the corresponding location 28 and thus of the tissue 3.

In particular, each output image 22, or each output pixel 26 within an output image 22, may be constituted of an output set 29 of spectral bands 30, which are termed output spectral bands in the following. The input set 15 and the output set 29 differ in at least one spectral band, that is preferably located in the visible light range.

Preferably, the spatial resolution of the output images 22 corresponds to, or is lower than, the spatial resolution of the input images 10. Thus, the size and location of the part of the object 2 that is represented by the input and output pixels 14, 26 match each other in the input and output images 10, 22. Alternatively, the output images 22 may contain less or more output pixels than the input images 14. In the former case, a plurality of input pixels 14 may be combined into an output pixel 26. In the latter case, an input pixel 14 may be copied onto a plurality of output pixels 26.

The medical imaging apparatus 1 may further comprise an image processor 31 for generating the output pixels 26 from the input pixels 14 and for replacing an input spectral signature 32 of an input pixel 14, which input spectral signature is represented by the input set 15, by an output spectral signature 34 in an output pixel 26, which output spectral signature is represented by an output set 29. The output pixel 26 which contains the replacement output spectral signature 34 corresponds with respect to its location and size in the output image 22 to the location and size of the input pixel 14 in the input image 10. The input spectral signature 32 corresponds to the intensity distribution in the input spectral bands 16 due to the changes in reflectance across the spectrum of each location 28.

The output spectral signature 34 of an output pixel 26 as represented by the spectral bands 30 of the output set 29 corresponds preferably at least to an approximation of the spectral signature 36 in the visible-light range 37 of the tissue 3 at the location 28 of the input pixel 14 in the field of view 12. Thus, the output images 22 contain a computed rendition of the visible color of the tissue 3 in the field of view 12, and thus render what would be seen by an observer if the input image 10 were captured in the visible light range 37. In each pixel of the output image 22, the input set 15 is replaced, at least partly, by the output set 29.

In particular, the input set 15 contains at least one input-only spectral band 38 which is not contained in the output set 19. Preferably, the input-only spectral band is located in the invisible-light range 18. In the output set 29, at least one output-only spectral band 39 is contained which is preferably in the visible-light range 37 and not contained in the input set 15. The replacement of the at least one input-only spectral band 38 by the at least one output-only spectral band 39 is done by the image processor 31. The image processor 31 can be realized in any combination of hardware and software or in hardware or software alone.

The medical imaging apparatus 1 may further comprise an illumination system 40 for illuminating the tissue 3 in the non-visible light range 18. The illumination system 40 is configured to generate light 42 containing at least the input spectral bands 16. The light 42 may be constituted of an illumination set 44 of illumination spectral bands 46 which at least comprise the output spectral bands 30. In one embodiment, the illumination set 44 may correspond to the input set 15.

The illumination 40 may be provided with a filter system 48 which may block the light 42 in the visible-light range and/or restrict the light 42 to the input spectral bands 16. In particular, the illumination system 40 may include one or more IR and/or NIR light sources.

The image processor 31 preferably comprises a spectral analysis module 50 which is configured to perform a spectral fitting to the input spectral signature 32 and to compute a tissue reference value 52 from the spectral fitting. The image processor 31 may be configured to retrieve or compute the output spectral signature 34, i.e. the intensity in the at least one output-only spectral band 39, in dependence of the tissue reference value 52. The tissue reference value is representative of the color of the tissue 3 in the visible-light range. In particular, the tissue reference value 52 may be representative of the content and/or concentration of particular biological pigments or chromophores in the location 28 of the tissue 3 that is mapped to the input pixel 14. The tissue reference value is a numerical value that can be a bit or a bit field. The tissue reference value can contain one or more quantities such as weighing factors, exponents of an exponential or Fourier series, or RGB values.

A storage member 54 of the medical imaging apparatus 1 may contain calibration data 56 which are used to map the input set 15 to the output set 29 and thus to render the actual spectral signature 36 of the object 2 in the output images 22. The calibration data 56 may represent parameters of a transfer function which allows computing an output set 29 from an input set 15. The calibration data may represent parameters of a teaching function or a neural network which has been trained with input sets 15 and matching output sets 29 for calibration purposes. The calibration data 56 may be a representation of various spectral signatures in the form of at least one spectral library 56. The representation may be in the form of numerical values which correspond to the intensities in the respective spectral bands of the color space defined by the input set 15 and the output set 29.

The storage member 54 may, in one embodiment, store representations of model input spectral signatures 58 of various biological pigments in the spectral library 56. The model input spectral signatures 58 may be restricted to the input spectral bands 16. The model input spectral signatures 58 may be used for spectral fitting the input spectral signature 32 of the input pixels 14 as represented by the input set 15. In spectral fitting, an algorithm may automatically select a set of model input spectral signatures 58 which in combination result in the closest approximation of a given input spectral signature 32 of an input pixel 14. This may be done for all input pixels of an input image 10. The particular linear or non-linear combination of model input spectral signatures 58 in a given input spectral signature indicates what types of biological pigments are present in the location 28 which is represented by the respective input pixel 14. The weight of a particular model input spectral signature 58 within the combination of model spectral signatures 58 needed to approximate the input spectral signature 32 is an indication of the concentration of the respective biological pigments in the location 28.

Alternatively or additionally, the spectral library 56 may comprise model output spectral signatures 60. The model output spectral signatures may be restricted to the at least one output-only spectral band 39. For each input spectral signature 32, the matching output spectral signature 60 is retrieved, e.g. by using the tissue reference value 52. From the model output spectral signature 60 the intensity in the at least one output-only spectral band 39 is determined which corresponds to the matching model input signature 58.

In another embodiment, the model output spectral signatures 60 stored in the spectral library 56 correspond to the output spectral signatures 60 of different biological pigments. The output spectral signature 34 of an output pixel 26 is, in such an embodiment, composed by the image processor 31 from the individual model output spectral signatures 60 of the biological pigments that have been found to contribute to the input spectral signature 32. The latter embodiment is explained in closer detail in the following.

The output spectral signature 34 of an output pixel 26 may be composed of a combination of model output spectral signatures 60. A model output spectral signature 60 and a model input spectral signature 58 may be assigned both to a particular biological pigment. The model output spectral signature 60 represents the spectral signature 36 of the biological pigment in the visible light range 37, in particular in the color space of the output image 22. The model input spectral signature 58 corresponds to the spectral representation of the biological pigment in the non-visible light range 18, in particular in the input spectral bands 16.

The output spectral signature 34 in the output image 22 may contain a combination of model output spectral signatures 60 which together form the output spectral signature 34 of the output pixel 26. The weight of the individual model output spectral signatures 60 in the output spectral signature 34 is the weight of the corresponding model input spectral signatures 58 in the input spectral signature 32. The material composition of the tissue 3 at the location 28 of the input pixel 14 as computed during the spectral fitting is used for composing the output spectral signature 34 in the visible-light range from the individual model output spectral signatures 60 of the constituent biological pigments.

The medical imaging apparatus 1 may further comprise an optical system 62 which is situated in the optical path 64 of the light 42 of the illumination system 40 and in the optical path 66 of the multispectral camera 8. Thus, the optical paths 64, 66 are aligned and a field of illumination, determined by an illuminator in which the illumination intensity is above a certain threshold, matches the field of view 12.

A beam splitter arrangement 70 may be used to separate the optical paths 64, 66.

A viewer 72 e.g. an ocular or binocular may also be provided to allow direct inspection of the field of view 12 through the optical system 62. The viewer 72 may have its own optical path 74 which is split off the optical path 64, 66 by the beam splitter arrangement 70. The display 24, or an additional display, may be arranged between the viewer 72 and the beam splitter arrangement 70 in the optical path 74.

The medical imaging apparatus 1 and its processes as described above, applies also if the input images 10 and the output images 22 are three-dimensional.

Figure 2:
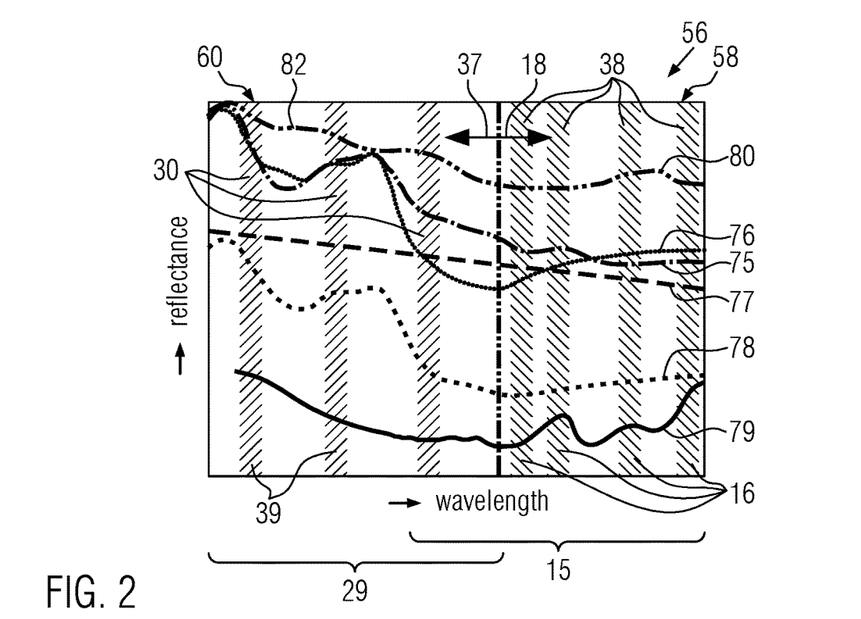
FIG. 2 shows a schematic rendition of spectra of biological pigments.

In FIG. 2, model input spectral signatures 58 in the non-visible light range 18 and model output spectral signatures 60 in the visible-light range 37 are shown for different biological pigments.

In FIG. 2, line 75 shows the model input and output spectral signatures 58, 60 of deoxy-hemoglobin, line 76 the model input and output spectral signatures of oxy-hemoglobin, line 77 the model input and output spectral signature of eumelanin, line 78 the model input and output spectral signature of blood with 80% oxygen saturation and line 79 the model input and output spectral signature of fatty tissue. The model input and output spectral signatures 75-79 are in the visible-light range 37 and the non-visible light range 18 respectively.

The model output signatures can be derived, in particular computed, by using calibration data 56, such as a spectral library. Other forms of calibration data are transfer functions, which map an input spectral signature onto an output spectral signature, or the parameters of a self-teaching computational structure such as a neural network, which is calibrated prior to the use of the apparatus 1.

In FIG. 2, the model input and output spectral signatures form a sample spectral library 56 for the indicated biological pigments. It can be seen that the model output spectral signatures 60 are simply a continuation or completion in the visible-light range 37 of the model input spectral signatures 58 in the non-visible light range 18.

The model input and output spectral signatures 75-79 are schematic representations on an arbitrary scale. The input spectral signature 32 of a given input pixel in the input spectral bands 16 is indicated exemplarily as line 80. In the spectral fitting a weighted sum of the model input spectral signatures 58 is computed, which approximates best, e.g. by minimizing the least-square error across the input spectral bands 30, the sample input spectral signature 80. The weights of the individual model input spectral signature 58 are then used to compute the sample output spectral signature 82 in the output spectral bands 30. The weights of the individual model spectral signatures 58 are simply applied as is to the model output spectral signatures 60.

As can be seen further from FIG. 2, the model input spectral signatures 58 can be determined from the input set 15 of input spectral bands 16. Once the model input spectral signature is identified (or the object or tissue is classified), the intensity in the at least one output-only spectral band 39 can be derived from the corresponding model output signature 60 (or classification). The intensities in the spectral bands 30 of the output set 29 then correspond to the colors of the object 2.

As can be seen from FIG. 2, at least one spectral band may be shared by both the input and the output set 15, 29.

Figure 3:
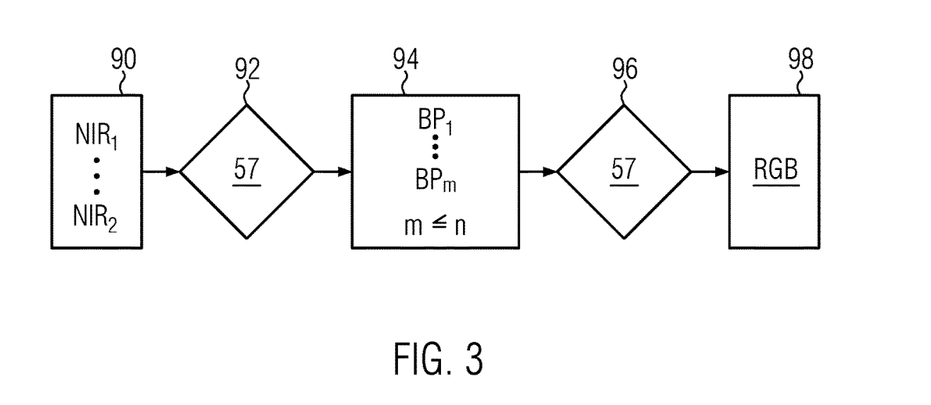
FIG. 3 shows a schematic rendition of the medical imagining method according to the invention.

With reference to FIG. 3, the medical imaging method is briefly described.

In an image acquisition 90, multispectral data $NIR_1$ to $NIR_n$ are obtained for each input pixel 14 in the input image 10 in each of the n input spectral bands 16 by the camera 8. The number n of input spectral bands 16 corresponds at least to the number m of biological pigments that are responsible for the color of the tissue 3 in the visible-light range.

By spectral fitting 92, the composition of model input spectral signatures from the spectral library 56 is computed that best matches the multispectral data $NIR_1$ to $NIR_n$. From the spectral fitting 92, the concentration of the biological pigments $BP_1$ to $BP_m$ in the tissue 3 at the location 28 is determined.

Figure 1:
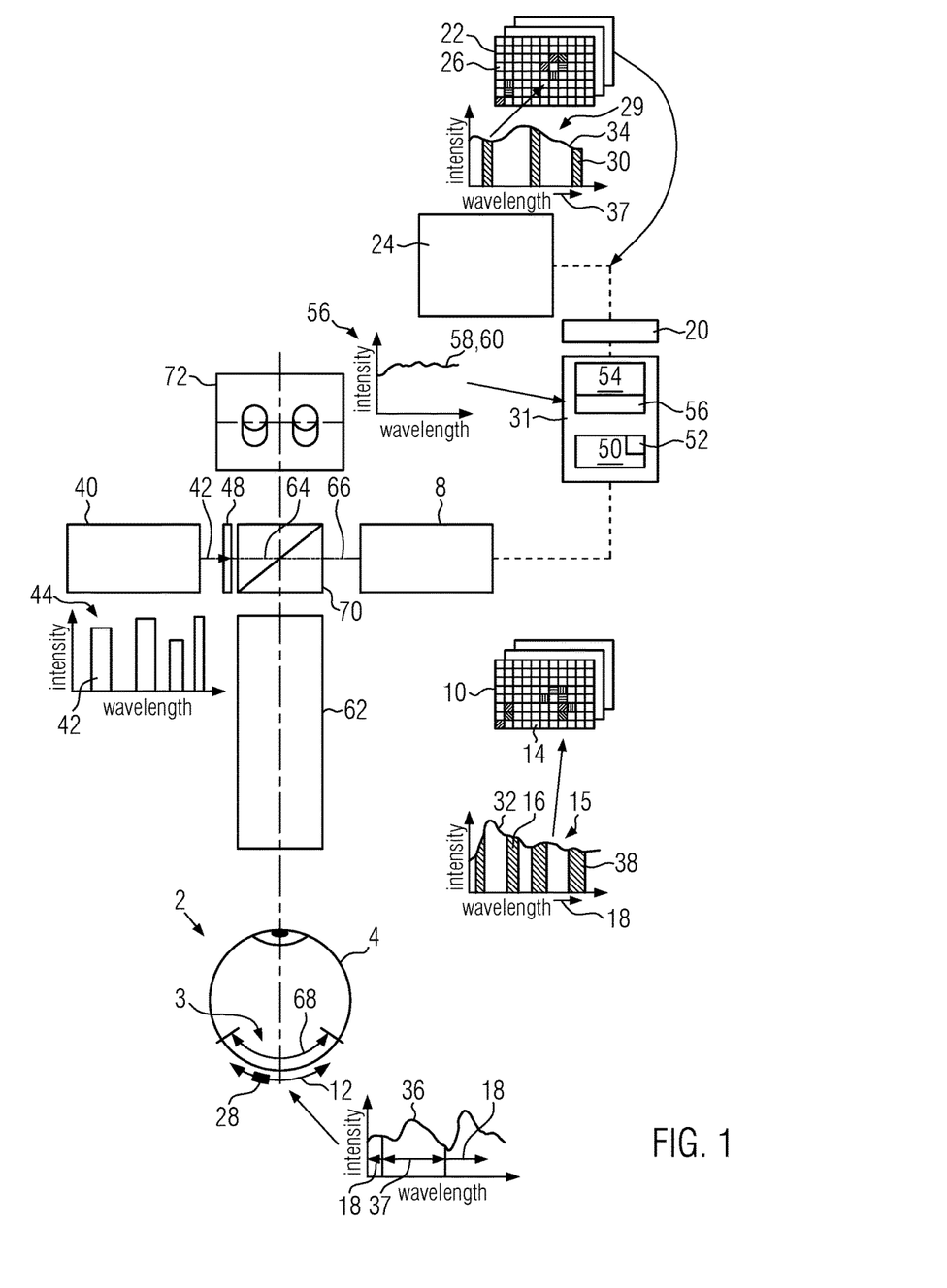
FIG. 1 shows a schematic rendition of a medical imaging apparatus according to the invention.

In the output image generation 96, the output spectral signature 34 is computed for each output pixel 26 corresponding to the input pixel 14 with respect to the location 28 in the field of view 12 (FIG. 1). The output spectral signature 34 at each output pixel 26 is composed of the individual model output spectral signatures 60 of the biological pigments BP1 to BPm determined to be present at the location 28 by the spectral fitting 92. The weight of the individual model output spectral signature 60 in the output spectral signature 34 corresponds to the weight of the model input spectral signature 58 in the input spectral signature 32. The model output spectral signatures 60 are looked up in a spectral library as are the model input spectral signatures 58.

Finally, in step 98, the output image 22 comprising the output pixel 26 is output in a color space format, such as RGB.

REFERENCE NUMERALS

1 Medical imaging apparatus
2 Object
3 Tissue
4 Eye
6 Ophthalmological imaging device
8 Multispectral camera
10 Input image
12 Field of view
14 Input pixel
15 Input set of spectral bands
16 Input spectral bands
18 Non-visible light range
20 Output interface
22 Output image
24 Display
26 Output pixel
28 Location of input pixel in field of view
29 Output set of spectral bands
30 Output spectral bands
31 Image processor
32 Input spectral signature as recorded by camera
34 Output spectral signature for output in the display
36 Actual spectral signature of object
37 Visible-light range
38 Input-only spectral band
39 Output-only spectral band
40 Illumination system
42 Light generated by illumination system
44 Illumination set of spectral bands
46 Illumination spectral bands
48 Filter system
50 Spectral analysis module
52 Tissue reference value
54 Storage member
56 Calibration data, such as spectral library
58 Model input spectral signature
60 Model output spectral signature
62 Optical system
64 Optical path of light of illumination system
66 Optical path of camera
68 Field of illumination
70 Beam splitter arrangement 72 Viewer
74 Optical path of viewer
75-79 Model input and output spectral signatures
80 Sample input spectral signature
82 Sample output spectral signature
90 Image acquisition step
92 Spectral fitting
94 Tissue composition determination
96 Output image generation
98 Image output step
NIR1, NIRn Multispectral data in each of n input spectral bands
BP1, BPm concentration of each of m biological pigments determined by spectral fitting

What is claimed is:

1. A medical imaging apparatus for the imaging of a light-sensitive object including biological tissue, the object having a spectral signature, the medical imaging apparatus comprising:
   a multispectral or color camera for capturing input images, the spectral signature of the object being represented in the input images by an input set of discrete spectral bands,
   an output interface for transmitting output images,
   wherein, in the output images, the spectral signature of the object in the visible light range is represented by an output set of discrete spectral bands,
   wherein at least one input-only spectral band in the input set is replaced by at least one output-only spectral band in the output set,
   the medical imaging apparatus further comprising:
      a storage member, in which calibration data are stored for mapping the input set to the output set, wherein the calibration data include representations of model input spectral signatures of a plurality of biological pigments in the input set of discrete spectral bands and representations of model output spectral signatures of the plurality of biological pigments in the output set of discrete spectral bands, and
      an image processor for determining an intensity in the at least one output-only spectral band depending on the input set and the calibration data, wherein the image processor is configured to determine a local concentration of at least one of the plurality of biological pigments in the tissue from the input set of an input pixel in at least one of the input images and assign the output set to an output pixel depending on the local concentration;
   wherein the output set contains a combination of at least a subset of the model output spectral signatures of the plurality of biological pigments, and
   wherein the image processor is further configured to map the input set to the output set by spectral fitting the spectral signature of the input set to the model input spectral signatures classifying the tissue based on the spectral fitting, deriving a tissue reference value from the calibration data based on the classifying, and determining the output set based on the tissue reference value.

2. The medical imaging apparatus according to claim 1, further comprising an illumination system for illuminating the object with light including an illumination set of spectral bands in which the at least one output-only spectral band is either attenuated in comparison to the remaining spectral bands or not contained.

3. The medical imaging apparatus according to claim 1, wherein the at least one input-only spectral band is located in the non-visible light range.

4. The medical imaging apparatus according to claim 1, wherein the illumination set contains at least one spectral band in the NIR range.

5. The medical imaging apparatus according to claim 1, wherein a majority of the spectral bands in the input set is located in the non-visible light range and a majority of the spectral bands in the output set is located in the visible light range.

6. The medical imaging apparatus according to claim 1, further comprising a spectral library, the spectral library comprising a set of the model output spectral signatures.

7. The medical imaging apparatus according to claim 1, wherein at least one of the input set and the illumination set represent light having a wavelength of at least 550 nm and comprising at least one of NIR and IR.

8. A medical imaging method for imaging a light-sensitive object including biological tissue of the eye, the object having a spectral signature, the method comprising the steps of:
   acquiring input images in an input set of discrete spectral bands, the input set representing the spectral signature in the spectral bands of the input set,
   transmitting output images including an output set of discrete spectral bands, the output set representing the spectral signature in the spectral bands of the output set,
   converting the input images to the output images by replacing at least one input-only spectral band in the input set by at least one output-only spectral band in the output set and adapting the intensity in the at least one input-only spectral band to the spectral signature using previously stored calibration data, wherein the calibration data include representations of model input spectral signatures of a plurality of biological pigments in the input set of discrete spectral bands and representations of model output spectral signatures of the plurality of biological pigments in the output set of discrete spectral bands, and
   determining a local concentration of at least one of the plurality of biological pigments in the tissue from the input set of an input pixel in at least one of the input images and assigning the output set to an output pixel depending on the local concentration,
   wherein the output set contains a combination of at least a subset of the model output spectral signatures of the plurality of biological pigments, and
   wherein the calibration data is stored for mapping the input set to the output set by spectral fitting the spectral signature of the input set to the model input spectral signatures classifying the tissue based on the spectral fitting, deriving a tissue reference value from the calibration data based on the classifying, and determining the output set based on the tissue reference value.

9. The medical imaging method according to claim 8, wherein the tissue is illuminated in the non-visible light range, the at least one input-only spectral band is located in the non-visible light range and the at least one output-only spectral band is located in the visible light range.

10. The medical imaging method according to claim 8, wherein an illumination of the object in the at least one output-only spectral band is weaker than in the at least one input-only spectral band.

11. The medical imaging method according to claim 8, further comprising the step of generating the output set from representations of stored model output spectral signatures.

12. A non-transitory computer storage media storing a program causing a computer to execute the method according to claim 8.

* * * * *